United States Patent
Keefe et al.

(10) Patent No.: US 8,948,478 B2
(45) Date of Patent: Feb. 3, 2015

(54) MULTI-MEDIA MEDICAL RECORD SYSTEM

(75) Inventors: Gary Keefe, Brecksville, OH (US); Richard Edwards, Akron, OH (US); Michael Kolberg, Hinckley, OH (US); Timothy Jablonski, Lakewood, OH (US)

(73) Assignee: Codonics, Inc., Middleburg Heights, OH (US)

( * ) Notice: Subject to any disclaimer, the term of this patent is extended or adjusted under 35 U.S.C. 154(b) by 202 days.

(21) Appl. No.: 13/270,124

(22) Filed: Oct. 10, 2011

(65) Prior Publication Data

US 2012/0177256 A1 Jul. 12, 2012

Related U.S. Application Data

(60) Provisional application No. 61/391,503, filed on Oct. 8, 2010.

(51) Int. Cl.
  *G06K 9/00* (2006.01)
  *G06F 19/00* (2011.01)
(52) U.S. Cl.
  CPC ............ *G06F 19/322* (2013.01); *G06F 19/321* (2013.01)
  USPC .............................................. 382/128; 705/3
(58) Field of Classification Search
  USPC ....................................................... 382/128
  See application file for complete search history.

(56) References Cited

U.S. PATENT DOCUMENTS

| | | | |
|---|---|---|---|
| 2006/0149601 A1* | 7/2006 | Langhofer et al. | 705/3 |
| 2008/0021740 A1* | 1/2008 | Beane et al. | 705/3 |
| 2008/0219523 A1* | 9/2008 | Brackett | 382/128 |

* cited by examiner

*Primary Examiner* — Hadi Akhavannik
(74) *Attorney, Agent, or Firm* — Pearne & Gordon LLP

(57) ABSTRACT

Disclosed is a method of processing data pertaining to a medical procedure. The method includes receiving information indicative of at least one of an imaging device and a video capture device, and information indicative of an identity of a patient to be treated during the medical procedure. The data is received by the computer system without the identity of the patient. A relationship is established to link the data with the identification of the patient. Application of at least one processing rule is initiated to reduce a file size of the data from an original file size of the data as transmitted by the at least one of the imaging device and the video capture device. The data is stored in combination with the identification of the patient in a manner compliant with a standardized medical imaging transmission format.

9 Claims, 3 Drawing Sheets

MULTI-MEDIA MEDICAL RECORD SYSTEM

CROSS-REFERENCE TO RELATED APPLICATIONS

This application claims the benefit of U.S. Provisional Application No. 61/391,503, filed Oct. 8, 2010, which is incorporated in its entirety herein by reference.

BACKGROUND OF THE INVENTION

1. Field of the Invention

This application relates generally to a method and apparatus for storing medical data and, more specifically, to a storage server and method for combining video data with medical records, and more specifically, to methods that optionally reduce the size of the video data and route the medical records containing video data, either manually or automatically, to a desired storage destination other than the storage server, and provide an interface to remotely access and view the medical records.

2. Description of Related Art

Conventional methods and apparatuses for storing medically related videos use analog media such as magnetic tapes or standalone digital video capture devices that are not integrated into healthcare EMR (Electronic Medical Record) systems and storage systems. With conventional systems, videos are usually stored on a single piece of removable media or one storage device that is not a part of the EMR system. This limits the ability to share video data with other healthcare professionals and increases the risk that videos will be lost or deleted. Additionally, videos from conventional systems are usually saved in a consumer file format such as MPEG that is not compatible with healthcare storage systems called PACS systems. MPEG files must be converted to a different format called DICOM that is a medical standard for encoding and transferring image, video and other data types within healthcare organizations. Once a video is converted to the DICOM standard, it can be transferred to a PACS system for long-term storage. While the DICOM standard defines support for videos, most PACS systems do not fully support video data. PACS systems are typically limited to transferring patient records containing video data in and out of the system. Most PACS systems also lack adequate storage and storage management for handling the large size of video data and are unable to view videos on DICOM display terminals that are primarily intended for image viewing. The challenge is to provide a solution that leverages existing healthcare IT (Information Technology) data networks and equipment that were not specifically designed to store and display medical records containing video data.

BRIEF SUMMARY

According to one aspect, the subject application involves a method of processing data that includes image data, video data, or image and video data pertaining to a medical procedure. The method includes using a computer system to receive a video identification indicative of at least one of an imaging device and a video capture device that is to be a source of the data captured during the medical procedure. A patient identification indicative of an identity of a patient to be treated during the medical procedure is received with the computer system. The data transmitted by the at least one of the imaging device and the video capture device is received with the computer system, and is received without the identity of the patient. A relationship is established to link the data with the identification of the patient. Application of at least one processing rule is initiated to reduce a file size of the data from an original file size of the data as transmitted by the at least one of the imaging device and the video capture device. The data is stored in combination with the identification of the patient in a manner compliant with a standardized medical imaging transmission format.

According to another aspect, the subject application involves a method of capturing data including image data, video data, or image and video data pertaining to a medical procedure. A computer system is used to receive a video identification indicative of a video capture device that is to capture the data during a medical procedure. With the computer system, a patient identification indicative of a patient to be treated during the medical procedure is also received. Information is transmitted over a communication network for establishing the patient identification at the video capture device that is to capture the data, thereby allowing the video capture device to associate the patient identification with the data. The method also includes receiving the data associated with the patient identification transmitted by the video capture device, and storing, in a computer-accessible memory, the data associated with the patient identification transmitted by the video capture device. A subsequent request for the data from the computer-accessible memory returns the data in combination with the patient identification.

According to another aspect, the subject application involves a method of processing data including image data, video data, or image and video data pertaining to a medical procedure. The method includes using a computer system, receiving the data in a standardized medical image transmission format. The standardized medical imagining transmission format includes a patient identification in combination with the data. Application of at least one processing rule is initiated to reduce a file size of the data combined with the patient identification from an original file size of the data as received by the computer system.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE DRAWINGS

The invention may take physical form in certain parts and arrangement of parts, embodiments of which will be described in detail in this specification and illustrated in the accompanying drawings which form a part hereof and wherein.

DETAILED DESCRIPTION

Figure 1:
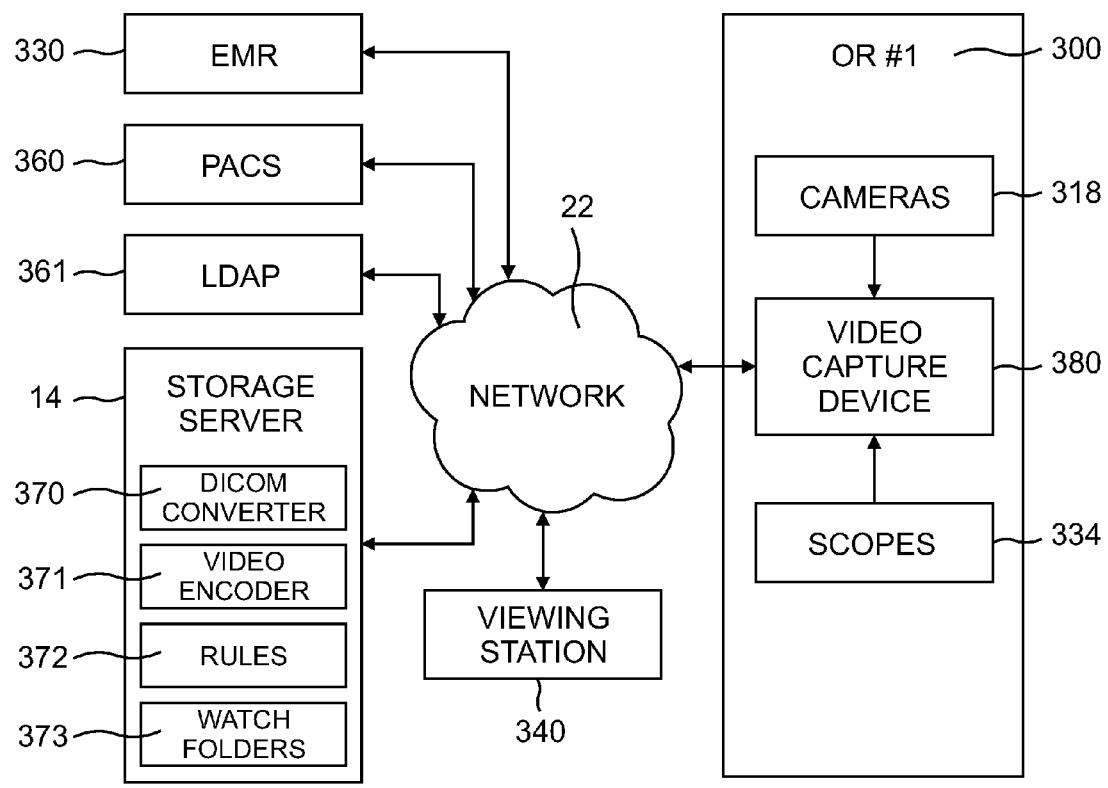
FIG. 1 is an illustrative embodiment of a computer system including a plurality of cameras for capturing video data to be received by a storage server and optionally processed for storage PACS or transmission over a communication network and/or for being displayed.

Certain terminology is used herein for convenience only and is not to be taken as a limitation on the present invention.

Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

A fully integrated digital medical video solution efficiently captures, identifies, stores, distributes and views video data as a part of patient healthcare records. This includes associating videos with the correct patient, physician and procedure identification information, compressing the size of the video data to accommodate the limitations of existing healthcare storage systems, limiting the bandwidth requirements for transferring and playback of videos to accommodate the capacity of existing data networks, and transmitting videos in a format that is compatible with viewing software on existing display terminals in healthcare environments. Access to patient medical records that include video are also managed in a way that complies with patient privacy guidelines without being a significant burden to healthcare personnel.

FIG. 1 shows an illustrative embodiment of a healthcare IT communication network 22 that can include a restricted, internal network for use within the healthcare organization, an external network such as the Internet, or a combination thereof. The network 22 operatively connects servers and other networkable devices including at least one EMR (Electronic Medical Record system) 330 that stores and provides patient identification information and stores patient healthcare records, at least one PACS (Picture Archiving and Communication System) 360 that stores and retrieves medical images and videos in standardized medical imaging transmission format, such as a format compliant with the Digital Imaging and Communications in Medicine ("DICOM") standard, at least one LDAP (Lightweight Directory Access Protocol server) 361 that stores and transmits clinician identification information, at least one storage server 14 that stores, assembles, processes, converts and manages videos and/or images, at least one operating room 300 with a plurality of video capture devices 380 for capturing and optionally recording videos and images from one or more video cameras 318 and medical scopes 334 (generally "imaging devices") containing video cameras, and at least one viewing station 340 that reproduces videos and images to be displayed to medical personnel. PACS 360 can optionally be dedicated for storing such data in the standardized format for subsequent retrieval over the network 22.

Each video capture device 380 can include a hard disk drive, flash memory, analog recording tape or other suitable non-transitory computer-readable medium on which data comprising video, image or video and image data captured by a camera 318, medical scope 334, or other connected imagining device is stored. A computer processor provided to the video capture device 380 can execute computer-executable logic to capture the video and/or image data as described herein. At the beginning of a medical procedure, the video capture device(s) 380 can be utilized to obtain patient identification information from a patient census database on the storage server 14. The patient census database stored by the storage server 14 can optionally be created and updated by monitoring admit-discharge-transfer ("ADT") codes transmitted from the EMR 330 over the network 22 to the storage server 14 as described in U.S. Provisional Patent Application Ser. No. 61/264,784. ADT codes are simple codes that are entered into the system in response to the progression of a patient through treatment. The ADT codes can optionally be transmitted over the network 22 each time they are updated in the EMR 330, periodically, or at any desired interval. According to alternate embodiments, the ADT codes stored by the EMR 330 can be queried by query requests submitted by the storage server 14. Regardless of how such ADT codes are used to create and update the patient census database, a first code is entered for each patient when the patient is admitted to a healthcare facility, and a second code is entered into the EMR 330 when the patient is discharged. A plurality of different codes are also entered into the EMR 330 for a patient at various stages of treatment between admission and discharge, such as when a patient is transferred between departments, offices, healthcare facilities, treating physicians or other personnel, etc. . . . ADT codes can optionally be automatically, without user intervention, entered over the network 22 in response to a triggering event such as transmission of a signal by an automated medical modality, for example. For other embodiments, the ADT codes can be entered over the network 22 manually, by personnel at the healthcare facility when certain milestones are reached over the course of treatment.

Regardless of how it is entered into the server 14, the patient information can optionally be provided to the video capture device 380 in response to a request submitted by the video capture device. The query request can optionally be initiated by a clinician using an interface on the video capture device 380. For example, one or more query requests, including but not limited to DICOM Modality Work List look up of patient information in the patient census database stored by the storage server 14, and proprietary search methods involving communications over the network 22 that allow a clinician to look up patient information in patient census on the storage server 14 using an interface on the video capture device 380 can be submitted to the storage server 14. These proprietary search techniques can be specific to certain models of video capture devices. The DICOM Modality Worklist, for example, is a standardized and defined DICOM-compliant query routine performed by medical modalities such as medical imaging equipment, video capture device, and other hardware typically encountered in healthcare facilities for example. The query utilizes a standard C-FIND search for patient demographic and study details over the network 22. By automating the query performed by a medical modality typing and other manual-entry mistakes can be minimized.

In response to submitting the query request to the server 14, the server 14 transmits a subset of patients satisfying the query request stored in the storage server 14 to the video capture device. For example, the clinician can specify via the user interface provided to the video capture device 380 that the patient's last name begins with the letter "B" and this information can be transmitted over the network 22 to be submitted as part of the query request to the server 14. In response to receiving such a query request, the server 14 can transmit all patients having a last name that begins with the letter "B." This subset of patient information transmitted to the video capture device 380 can be displayed to the clinician via a display device provided to the user interface, for example, as a list the clinician can scroll through to locate the proper patient that will be the subject of the medical procedure. Once the correct patient identification information has been confirmed by the clinician using the video capture device 380, the information is maintained on the video capture device 380 during the procedure and sent to the storage server 14 along with videos and/or images to ensure the correct patient is associated with the videos and images.

Although search and selection of patient identification information is commonly performed by a clinician using the interface provided on many video capture devices 380 as mentioned above, an alternate method for identifying the patient information and combining it with videos and images is described in U.S. Provisional Patent Application Ser. No. 61/264,784, which is incorporated herein in its entirety by reference. The alternate method allows a clinician to use a data terminal included in the computer system operatively connected via network 22 or other networked computer to connect to storage server 14 and search then select the patient identification information on the storage server 14. The clinician also selects the video capture device 380 from a set of video capture devices known to the storage server 14. The storage server 14 has been configured with a set of known video capture devices and the associated network addresses. The storage server 14 can then use the network address of the video capture device 380 to associate the patient information with the videos and images. Additionally, the set of known video capture devices 380 can be configured on the storage server 14 with a symbolic name such as OR1 or ENDOSCOPY SUITE 2B that can be used to identify the specific video capture device 380. This method of patient information lookup and selection allows the video capture device 380 to send videos and images that do not contain any identifying patient information data or incomplete/inaccurate patient identification information to the storage server 14 where the software executed by the storage server 14 uses network address or symbolic name of the video capture device 380 to associate the patient information with the videos and images.

In alternate embodiments, patient information identification can be assigned by a clinician using a data computer terminal connected to the network 22 or other networked computer to connect to storage server 14 to search and select the patient identification information on the storage server 14. The clinician also selects the video capture device 380 from a set of video capture devices known to the storage server 14. The storage server 14 has been configured with a set of known video capture devices and an associated shared network folder name, sometimes called a "watch folder" for each known video capture device that will be sending videos and images. Additionally, the set of known video capture devices 380 and their associated shared network folders can be configured on the storage server 14 with a symbolic name such as OR SUITE 3A or ENDOSCOPY ROOM 1 that can be used to identify the specific video capture device 380 that will be sending the videos and images. Once the patient information is assigned by the clinician, the video capture device 380 stores videos and images into the shared network folder that is configured on the storage server 14 for that video capture device 380. The storage server 14 uses the shared network folder to associate the patient information with the videos and images. According to each of the embodiments, a relationship is established between the selected video capture device(s) 380 and the selected patient information so that the data captured by the video capture device 380 is stored in association with the selected patient information. Once stored, the patient information can be integrated with the captured data in a manner that makes the patient information inseparable from the captured data. According to alternate embodiments, the captured data can be stored with the patient information in a manner compliant with the DICOM standard.

Another aspect of the invention relates to assigning the identification information of the physician (e.g. full name, network username or email address) performing the procedure to the medical record containing videos and images. Rather than manual, typed entry of a physician's name, the physician's name is selected directly from a database of physicians stored on an LDAP 361 server on the network 22 who are authorized to treat patients at the healthcare facility. The LDAP 361 is accessible using the video capture device 380 or other computer terminal via the network 22. This will provide an authoritative source of information. The LDAP 361 server may optionally store a database of all users authorized to access the network 22 rather than, or in addition to the names of authorized physicians. The information in the LDAP 361 server can include the full name, network login username and email address of authorized personnel. Access to information contained on the LDAP 361 server usually requires those accessing the LDAP 361 to enter a username and password, thereby uniquely identifying those who log in. The storage server 14 can also be assigned a username and password to access the LDAP 361 server for the purpose of searching for physician information or other user information that may be retrieved for inclusion in medical records. The storage server 14 can optionally automatically log into the LDAP 361 server over the network 22 using the username and password assigned to the storage server 14 and provide an interface for a clinician using a data terminal, network computer or viewing station 340 on the same network 22 to search for a physician or other user on the LDAP 361 server. Once the desired physician or user is found and selected, the clinician selects the video capture device 380 from a set of video capture devices known to the storage server 14. The storage server 14 has been configured with a set of known video capture devices 380 and the associated network addresses. The storage server 14 uses the network address of the video capture device 380 to associate the physician information with the videos and images. Additionally, the set of known video capture devices 380 can be configured on the storage server 14 with a symbolic name such as OR1 or ENDOSCOPY SUITE 2B that can be used to identify the specific video capture device 380. This method of physician information lookup and selection allows the video capture device 380 to send videos and images that do not contain physician identifying information to the storage server 14 where the software on the storage server 14 uses network address or symbolic name of the video capture device 380 to associate the physician information with the videos and images.

In alternate embodiments, physician identification can be assigned by a clinician using a data computer terminal on the network 22 or networked computer to connect to storage server 14 to search and select the physician information on the storage server 14. The storage server 14 will be configured with a username and password to access the LDAP 361 server for the purpose of searching for a physician or other users that may be required for medical records. The storage server 14 can automatically log into the LDAP 361 server over the network 22, optionally in the background and out of view of the clinician, and provide an interface for a clinician using a data terminal on the network 22 or networked computer or viewing station 340 to search for a physician or other user on the LDAP 361 server. Once the desired physician or user is found and selected, the clinician selects the video capture device 380 from a set of video capture devices known to the storage server 14. The storage server 14 has been configured with a set of known video capture devices and an associated shared network folder name, also known as a "watch folder", for each known video capture device that will be sending videos and images. Additionally, the set of known video capture devices 380 and their associated shared network folders can be configured on the storage server 14 with a symbolic name such as OR SUITE 3A or ENDOSCOPY ROOM 1 that can be used to identify the specific video capture device 380 that will be sending the videos and images. Once the physician information is assigned by the clinician, the video capture device 380 stores videos and images into the shared network folder that is configured on the storage server 14 for that video capture device 380. The storage server 14 uses the shared network folder to associate the physician information with the videos and images.

As videos and images are transferred from the video capture devices 380 to the storage server 14 over the network 22, the videos and images are optionally processed according to rules 372 that are stored by the storage server 14. When so configured, multiple rules 372 can be applied to any given video, image or patient record on the storage server 14. Rules 372 can also be applied at different times in the processing for information. For example, some rules 372 may apply to video files are they are received in watch folders while other rules 372 are applied to converter the videos to patient records in DICOM format or transfer patient records of the network 22 to other systems such as PACS 360 servers. The rules 372 can optionally govern a method of compressing the size of captured video data and route predetermined video data to various long-term storage destinations such as PACS 360.

Data produced from modern video capture devices 380 that are connected to high definition video sources from cameras 318 and scopes 334 can exceed 15 GB of data storage per hour of video. Many healthcare facilities lack sufficient storage requirements for long-term archiving of large videos on PACS 360 servers. Compressing videos using automatic, rule based processing is a convenient method of managing the data storage requirements without burdening healthcare professionals with manual editing or compressing of videos.

One application of the rules 372 configured on storage server 14 is to allow each healthcare facility to define specific video "transcoding" settings based on the characteristics of the video received from the video capture device 380 or videos contained in patient records received from other sources such as PACS 360. Transcoding can be used to reduce the size of videos from the size captured by the video capture device 380 by decoding the source video into individual frames, then encoding those frames with new settings that generally include lower resolutions, lower bit rates, lower frame rates and improved compression algorithms. The rules 372 in the storage server 14 allow a single source video to be transcoded into multiple videos of reduced size. This is often desirable since different applications require different resolutions. For example, a physician preparing a presentation for a medical conference of a new surgery technique may want a high resolution video to show exceptional detail. A surgeon reviewing a surgery at home by retrieving video of the surgery stored in the PACS 360, storage server 14 or other network-accessible computer-readable medium over a DSL line with limited bandwidth, for example, may need a lower resolution and lower bit rate to avoid delays caused by the slower DSL network speed. A facility can configure any number of video transcoding rules 372 on the storage server 14, but a typical high definition video that is 1080p (1920×1080 resolution, 30 frames/second, 15 Mbits/second) will get transcoded to two or three smaller sizes including medium resolution of 480p (720×480 resolution, 30 frames/second, 2.5 Mbits/second) which is similar to DVD quality and a low resolution of 240p (360×240 resolution, 15 frames/second, 0.7 Mbits/second). In addition to changing the resolution, frame rate and bit rate, the rules 372 allow a different video compression technique to be used. This is commonly called an "encoding". MPEG2 is a popular video encoding method found in consumer and commercial applications that was used in many first or second generation medical video capture devices 380. New encoding techniques such as H.264 can reduce storage requirements by up to 25% of the original MPEG2 data size without a visually-noticeable change in video quality. The storage server 14 includes several video encoders 371 that can be combined with other settings including resolution, frame rate and bit rate in the rules 372.

Another method used to reduce the data storage requirements of a video is to eliminate parts of the video that have little or no clinical significance. For example, in some surgical procedures, only a few minutes of a one hour video may be considered important enough to archive. Having a simple, automatic method to identify the important sections of video can greatly reduce storage requirements. One method to accomplish this is to use a "marker" that is placed by the surgeon as a reference point to make a video clip around. The video capture device(s) 380 can include a foot pedal or thumb switch connected to a scope 334, for example, that is used by the surgeon to capture an image for documentation purposes during the procedure. These images typically include a time index that indicates the time in the video that the image was captured. A rule 372 can be configured on the storage server 14 that extracts a video clip from the corresponding video using a site specified number of seconds before the image time index and a different setting for the number of seconds after the image time index to use when extracting the video clip. Both the "before" and "after" configurable time settings are a part of the rule 372. For example, if an image was captured by the surgeon 30 minutes into a procedure and the storage server 14 had a rule configured to extract 120 seconds before the image and 60 seconds after the image, a clip of 3 minutes would be create by the storage server 14 by extracting video from time index 28 minutes to time index 31 minutes.

Another method to reduce the data storage requirements of videos is to manually extract clips from a video. Given the large size of some videos, it is impractical to move or manipulate a high-resolution video across a network. In this case, a rule 372 can be created on the storage server 14 to automatically generate a low-resolution video from the original high-resolution video on the storage server 14. In another aspect of the invention, a user accesses the storage server 14 from a viewing station 340 using a web interface or other graphical application on the viewing station over the network 22 to view the low-resolution video and create a list of start time and end time indexes that are used by the storage server to extract clips from the high resolution video. Alternately, a frame count index can be used instead of the time index to correlate the position in a low resolution video with the same approximate position in the high resolution video. In this way, the user is not burdened by the problems associated with viewing a high-resolution video, but can still accomplish the goal of extracting high-resolution clips using a low-resolution version of the video which is easier to view and navigate remotely.

In another embodiment of the invention that relates to video clips, rules 372 can be created on the storage server 14 that apply the same time indexes generated from automatic or manual video clipping, to be used for extracting clips from other videos of the same patient record. This allows video clips of a significant event to be generated from multiple points of reference using different cameras 318 or scopes 334 that were all captured at the same time in the same procedure.

Rules 372 can also be used to determine which videos and images will be transferred from the storage server 14 to other medical storage devices such as a PACS 360. One common application is to create a rule 372 that only transfers a specific resolution of any video to the PACS. For example, a rule 372 can be created that specifies to only transfer the 480p resolution of a video to the PACS. Rules 372 can also include patient, physician and/or procedure information in the decision making process when determining what medical records are selected for transfer or other operations. For example, a particular surgeon may want all their automatically generated video clips and images from gall bladder surgeries to be saved to PACS 360.

Rules 372 can be created to determine how long a video of a particular resolution, frame rate or bit rate will be saved on the storage server 14. Different rules 372 can be created for different time frames. For example, a rule can be set up on storage server 14 to delete all 1080p high resolution videos immediately after transcoding to lower resolutions 480p and 240p. A second rule 372 can be created on the same storage server 14 to delete all 480p videos 60 days after the last time they were viewed over the network 22 from a viewing station 340. Rules 372 can also include patient, physician and/or procedure information in the decision making process when determining what medical records are selected for deletion or other operations.

Multiple rules 372 can be created on the same storage server 14, that work in combination to increase their usefulness and power. There is no limit to the number of rules 372 that can be created on the same storage server 14. For example, a rule 372 can be created to transcode all videos to 480p. A second rule 372 can be created move all 480p videos on storage server 14 to a PACS 360. A third rule can be created to remove the 480p videos from the storage server 14, ninety days after the last time they were viewed over the network 22 from a viewing station 340.

Another aspect of the invention is the ability to capture and save individual images from a video. These images are sometimes called "still captures" or "still capture images". The purpose is to allow a user to create a set of one or more images that can be used for documentation in the patient healthcare record, verification of a procedure or event for billing purposes, education and training of new medical personnel, or as a tool for collaboration between medical professionals. Creating a still capture image after the procedure is complete, is sometimes necessary when some or all of the required still images were not captured by the surgeon at the time of the procedure using the foot pedal or thumb button on the scope 334. Creating still images from a video starts with a user logging into a storage server 14 from a viewing station 340 over the network 22. Using a graphical interface, such as a web interface, the user selects a video to be used for capturing still images. Given the large size of some videos, it is often impractical to move or manipulate a high-resolution video across a network. In this case, a rule 372 can be created on the storage server 14 to automatically generate a low-resolution video from the original high-resolution video on the storage server 14. The user can view the low-resolution video from the viewing station 340 and identify an area of interest in the video. The graphical interface for viewing the video on the viewing station 340 can include a "scrub bar", "fast forward", "fast backward", "single frame step", "multi-frame step", or other such interface element that allows the user move forward or backward through the video to locate an area of interest. Another method to locate an area of interest is to place graphical markers that represent previous still capture images as visual markers on the graphical interface. This feature typically uses the time index of the image, relative to the video it was captured from, to put visual marks that are placed on the scrub bar or other video timeline displayed on the graphics interface so the user can see the approximate position within the video that the image was created or extracted. For example, if a video is one hour in length and a still capture image was made from that video with a relative time index of 30 minutes from the start of the video, then a visual mark would appear in the middle of the scrub bar or timeline which is 50% of the way through the video. Using visual markers of previous still images can be a useful aid to quickly navigate through a video. Once an area of interest is located, the user can use controls on the graphical interface to fine tune the frame to be captured by moving the through the video using "single frame step forward", "single frame step backwards", "multi-frame step forward", "multi-frame step backward" or other such interface elements that allow the user move forward or backward through the video with greater precision than a scrub bar. Since the user is viewing a low resolution version of the video that was transcoded from a high-resolution video on the storage server 14, the level of detail required to correctly select a still capture image may not be visible from the low resolution video. To compensate for this, the storage server 14 includes software that uses the time index or frame count index of the low resolution video frame the user is viewing to extract the closest corresponding frame from the high resolution video as a separate image. The high resolution image is then displayed on the graphical interface of viewing station 340 so the user can see a greater level of detail and determine if the image should be captured and saved as part of the procedure. Each time the user navigates to a new video frame on the low resolution version, a corresponding high-resolution image is extracted from the high-resolution video on the storage server 14 and displayed on the viewing station 340.

In another embodiment of the invention, multiple storage servers 14 can be combined on the same network 22 to transparently aggregate the operation of the servers from the perspective of the user. When multiple storage servers 14 are aggregated together, the servers can share information related to patient records and optionally, other capabilities such as resources related to data storage, processor, job queues, workload, etc. A user can connect to any storage server 14 in the aggregation set from a viewing station 340. When the initial connection is made, the user will be presented with a login screen from the specified storage server 14. For purposes of simplifying this description, the storage server 14 that the user chose to log into will be called the "master server" and the other servers in the aggregation set will be called "remote servers". When a search for patient records is initiated by the user on the master server, the master server will notify all remote servers in the aggregation set over the network 22 to search for patient records using the same search parameters. Results from each remote server are received by the master server over the network 22 and the results are combined by the master server and displayed to the user on the viewing station 340. When the user selects a patient record, the master server will process the request locally if the patient record is on the master server, or pass control to the remote server that is storing the selected patient record. There are multiple methods to pass control to a remote server, including but not limited to, creating a URL, also known as a network link, containing the network address of the remote server and a unique indentifying information string for the patient record that the user selected on the viewing station 340 to transfer control to the remote server containing the patient record. The URL can also contain optional security information that is encoded into the URL string to prevent unauthorized users from accessing the storage server 14 with the same URL link from other computers on the network 22. The security information can use one or more methods to safeguard the storage server 14 including, but not limited to, the use of a timestamp, the use of a one-time access code, the use of a private/public key, and the encoding of unique identification information for the view station 340.

The method mentioned above for transferring control from a master server to a remote server can also be adapted to provide a method for a viewing station 340 to view a video stored in a patient record on a PACS 360. Many viewing stations 340 include DICOM image viewing software, sometimes called a DICOM viewer, that are not capable of viewing videos contained in DICOM patient records. Many PACS 360 servers can store and transfer DICOM patient record containing videos, but cannot extract the videos and provide a method to view them on a viewing station 340 that has a DICOM viewer without video viewing capabilities. This problem can be solved by providing an intermediary system, such as the storage server 14, that can retrieve a DICOM patient record containing a video from the PACS 360 and extract and send the video from the patient record to the viewing station 340 that has a video viewer installed that does not require a DICOM viewer. One method of accomplishing this functionality involves either the PACS 360 system or the viewing station 340 executing computer-executable instructions to create a URL, also known as a network link, with the network address of the storage server 14 and unique indentifying information for the patient record on the PACS 360. The URL can also contain optional encoded security information that prevents unauthorized users from accessing the storage server 14 with a URL link from other computers on the network 22. The security information can use one or more methods to safeguard the information on the storage server 14 including, but not limited to, the use of a timestamp, the use of a one-time access code, the use of a private/public key, and the encoding of unique identification information for the view station 340. The URL is presented to the user by the viewing station 340. The URL may not be directly visible to the user and may be "hidden" behind a graphical icon or other text message that is selected by the user. When the user selects the URL, either directly or indirectly, a web browser is launched on the viewing station 340 that transfers control to the storage server 14. When the URL is received by the storage server 14 and validated as authentic using the encoded security information, the storage server 14 retrieves the patient record from the PACS 360 using the unique patient record identifying information encoded in the URL and extracts the video data. The storage server 14 then sends the video data over the network 22 to a video viewing program on the viewing station 340. The video data can optionally be sent to the viewing station 340 using a secured network connection that employs an encryption technique to prevent unauthorized "ease dropping" on the video or other data being exchanged between the devices on the network 22. This technique permits a user to watch a video contained in a DICOM patient record when neither the PACS 360 nor the viewing station 340 is configured with software that can extract and play the video contained in the DICOM patient record.

The method described above for viewing videos contained in patient records on PACS 360 systems using a viewing station 340 can be simplified and used for viewing videos stored on the storage server 14. One such method involves having the storage server 14 incorporate a web server that is accessed from viewing station 340 over the network 22. After a user logs into the storage server 14 and selects a patient record contained on the system, the system can extract the video from the patient record if the patient record is in DICOM format, or directly access the video in the case where the video is a standalone file that is in not encapsulated in DICOM format. Accessing the video directly is an optimization that can reduce the amount of processing and time required to start playing the video. Once the storage server 14 has access to the video data, it sends the video data over the network 22 to a video viewing program on the viewing station 340. This technique permits a user to watch a video contained on the storage server 14. The video data can optionally be sent to the viewing station 340 using a secured network connection that employs an encryption technique to protect against unauthorized "eavse dropping" on the video or other data being exchanged between the devices on the network 22.

Video and image data contained in patient records on the storage server 14 can be downloaded by users on viewing stations 340 or other computer systems connected to the network 22. After the user logs into the storage server 14 from a viewing station 340 over the network 22, the user can select a patient study for downloading. The storage server 14 will extract the videos and images from the patient record, which is typically in medical format such as DICOM, and convert them to a common file format for more convenient use after the download is complete. The user will be presented with an interface on the viewing station 340 to select the specific video and image files to be downloaded and common file format to be used. Typical common file formats include, but are not limited to MPEG, AVI, WMV for videos and JPEG, BMP, PNG for images. A user option to download the files in Microsoft® PowerPoint® format will optionally be provided that combines all the images and videos selected by the user for downloading into a single file. The user can optionally specify that the images and videos are to be scaled to a same resolution for more convenient viewing after they are downloaded. Alternately, the user can chose to select a common "packaged" filed format such as ZIP, RAR, TAR or other formats that allow multiple files to be encapsulated in a single file for easier downloading.

Figure 2:
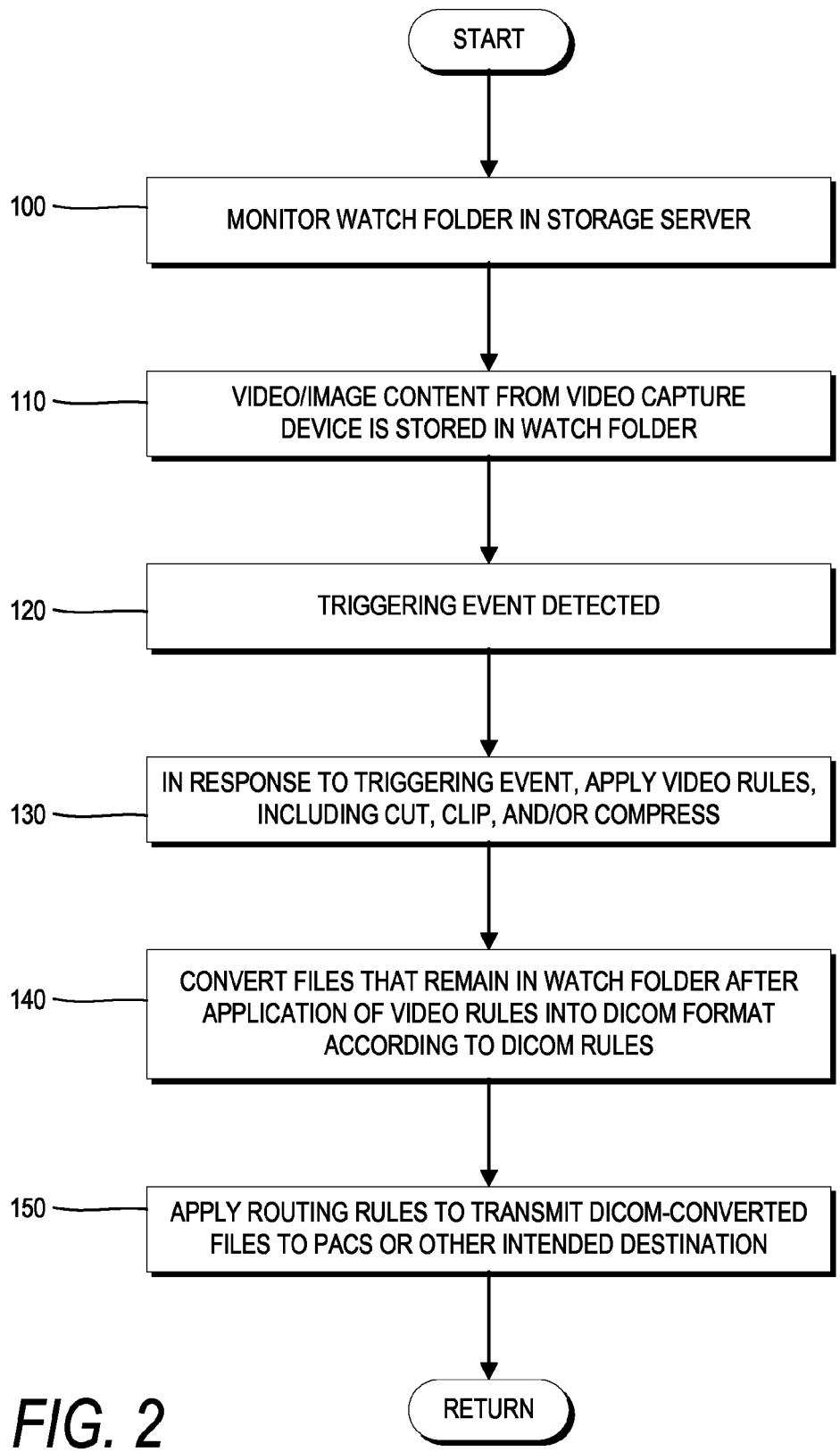
FIG. 2 is a flow diagram schematically illustrating a method of applying a rule to image data.

To further reduce the size of video and other data delivered to the PACS system at a given time, a predetermined set of rules can be applied to such data as it is received in a designated temporary storage folder in which video data is received for each local storage or on the storage server 14 or en route to the PACS 360 system or another DICOM device on the network 22. This temporary storage folder is accessible over a LAN, WAN, or a combination thereof, and is referred to as a "watch folder" 373 that is provided to the storage server 14. With reference to FIG. 2, the contents of the watch folder 373 are monitored for any changes at step 100. As the video data from the video capture device 380 occasionally arrives in the watch folder 373 at step 110, such a triggering event is detected at step 120. Detection of the triggering event can result in the automatic, and without user intervention, application of video-specific rules governing the management of video data received in the watch file 373 at step 130. The video-specific rules that can be applied to the video files in the watch folder 373 include, but are not limited to, at least one of: cutting, clipping, compressing (also known as transcoding) and deleting the video data.

Cutting the video data, as the name suggests, refers to deleting unwanted or irrelevant video data altogether. Clipping, refers to extracting and saving the portions of video data that are of interest and deleting the other, unwanted portions of the video data. And compressing refers to reducing the video one or more aspects of the video data including the resolution, frame rate, bit rate, encoding method to make the overall size of the video data smaller than it was originally.

When a storage server 14 is configured with video-specific rules 372, the application of the video-specific rules 372 typically results in less video data remaining in the watch folder 373 relative to the amount of data that was present before application of the rules. The video data that remains is converted according to DICOM rules at step 140 using the DICOM converter 370 in the storage server 14 into DICOM-compliant video data, and the DICOM-compliant video data is subsequently subjected to routing-specific rules and transmitted for storage in the PACS system or other intended storage destination at step 150.

The DICOM converter 370 can also convert image files received in the watch folder 373 into DICOM-compliant format and incorporate the images into the appropriate patient record.

To reduce the amount of time a user must wait for the storage server 14 to process a large video, the watch folder 373 can receive segments of video file. Each segment is processed after it is received according to the video-specific rules 372. After each segment is processed, it is saved until the last segment is received. When the last segment is received and processed, the complete video is assembled from the segments. The storage server 14 then processes the complete video the same as any other video. This technique reduces the amount of time a user must wait for a video to be ready for use.

Figure 3:
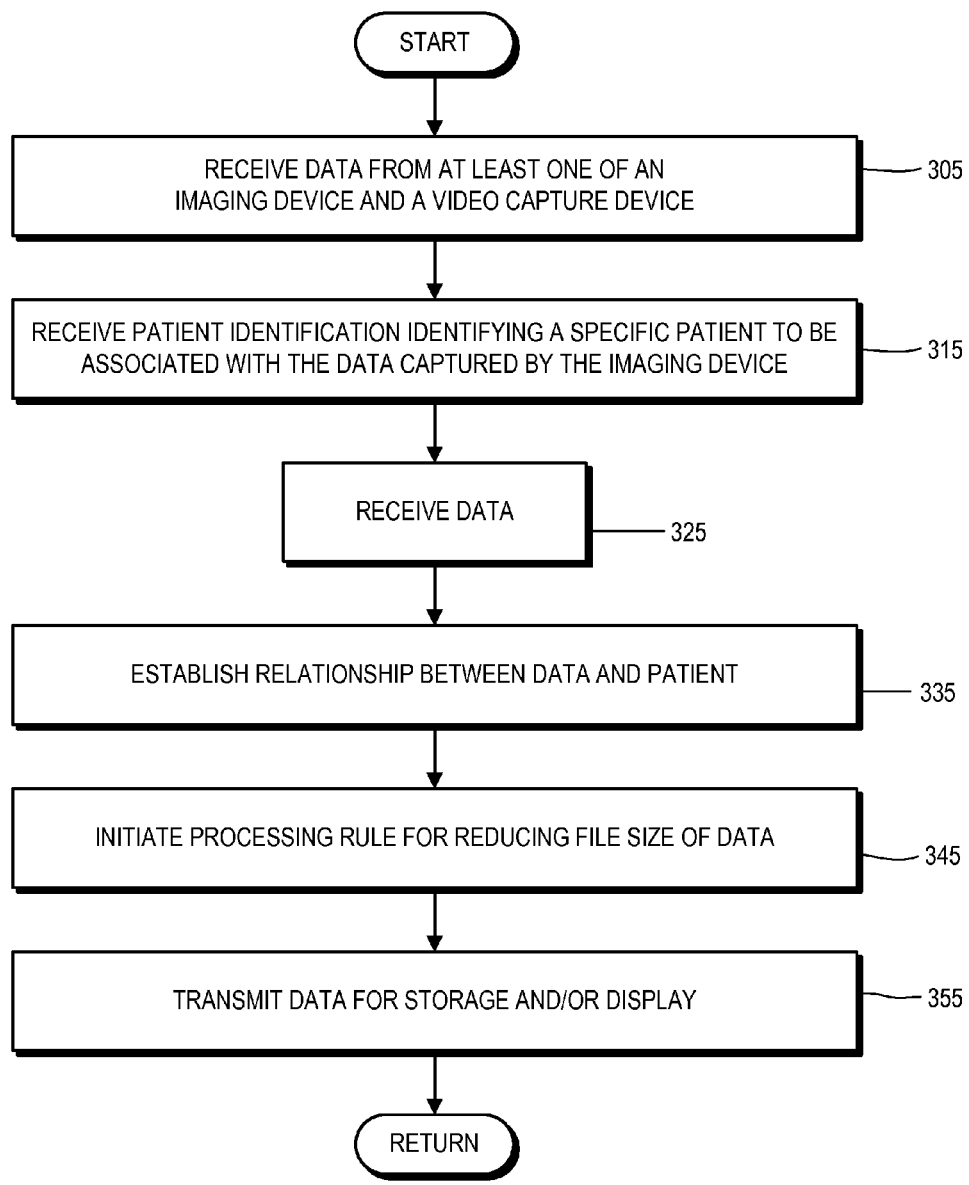
FIG. 3 is a flow diagram schematically illustrating a method of processing data including image data, video data, or a combination thereof.

An illustrative method of processing data such as image data, video data, or image and video data pertaining to a medical procedure is schematically illustrated in FIG. 3. The method includes receiving a video identification indicative of at least one of an imaging device and a video capture device that is to be a source of the data captured during the medical procedure at step 305. For the sake of brevity, video identification is to be received by the video capture device 380, and the data is to be received from the imaging device. However, it is to be understood that a networked computer terminal provided to the computer system can optionally execute computer-executable instructions to perform the method herein rather than the video capture device 380 of the computer system. Thus, the video capture device can optionally combine the patient information with the data as part of the process of preparing a DICOM or other standard-compliant data to be transmitted for storage in an enterprise storage location such as PACS 360. Alternate embodiments involve receiving the data from the video capture device 380 with such a computer terminal to be subsequently combined with the patient data. However for the present example, the method described below involves combining the data and patient information at the video capture device 380, to be subsequently stored in an enterprise storage solution such as PACS 360, and/or displayed to the clinician.

A patient identification indicative of an identity of a patient to be treated during the medical procedure is received at step 315. As described above, the patient identification can be selected from a list of patients, optionally a subset of patients satisfying a search criterion for example, via a user interface provided to the video capture device 380. The data transmitted by the imaging device is also received at step 325 by the video capture device 380 and optionally stored, at least temporarily, thereon. The data transmitted by, and received from the imaging device lacks (i.e., is without) the identity of the patient. In other words, the data can optionally be raw data such as that transmitted by a conventional video camera, for example.

A relationship is established at step 335, linking the data with the identification of the patient received by the video capture device 380. The relationship can be any association connecting the data to the patient. For example, the patient identification can be combined with the data such that, once the combination is stored, subsequently retrieving the data necessarily retrieves the patient identification. In other words, the patient identification is combined with the data such that the identification of the patient becomes a part of the data and cannot be inadvertently separated from the data when stored in a computer-accessible memory. According to alternate embodiments, the patient identification can be included in a header of the data, or otherwise combined in a manner compliant with the DICOM standard.

At least one processing rule can be initiated at step 345, reducing a file size of the data from an original file size of the data transmitted by the imaging device and/or video capture device. For example, transcoding the data can be initiated as a processing rule. The data can be transmitted at step 355 for: storage in combination with the identification of the patient in a manner compliant with a standardized medical imaging transmission format on a PACS 360 or other enterprise storage solution, being displayed by a display device, or a combination thereof.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method of processing data comprising image data, video data, or image and video data pertaining to a medical procedure, the method comprising:

using a computer system, receiving a video identification indicative of at least one of an imaging device and a video capture device that is to be a source of the data captured during the medical procedure that is to be processed;

with the computer system, receiving a patient identification indicative of an identity of a patient to be treated during the medical procedure, wherein said receiving said patient identification comprises:

receiving a query request for said patient identification from the video capture device over a communication network; and searching a database of electronic medical records of patients for said patient identification satisfying said query request;

with the computer system, receiving the data transmitted by the at least one of the imaging device and the video capture device, wherein the data is received without the identity of the patient;

establishing a relationship that links the data with the identification of the patient after receiving the data from the at least one of the imaging device and the video capture device over the communication network;

initiating application of at least one processing rule that, when complete, reduces a file size of the data from an original file size of the data as transmitted by the at least one of the imaging device and the video capture device; and storing the data in combination with the identification of the patient m a manner compliant with a standardized medical imaging transmission format.

2. The method of claim 1 further comprising storing, in a computer-accessible memory, the data captured by the at least one of the imaging device and the video capture device related to the patient identification.

3. The method of claim 1 further comprising:
after receiving the data transmitted by the at least one of the imaging device and the video capture device over a communication network to be received by the computer system, initiate transcoding of the data utilizing the computer system.

4. The method of claim 1, wherein said establishing the relationship comprises:
receiving an identity of a target folder in which the data captured by the video capture device is to be at least temporarily stored; and
assigning the patient identification to the data stored in the target folder.

5. The method of claim 1, wherein the patient identification is combined with the data such that the identification of the patient becomes a part of the data and can not be inadvertently separated from the data when stored in the computer-accessible memory.

6. The method of claim 1 further comprising storing, in a computer-accessible memory, the data transmitted by the at least one of the imagining device and the video capture device with the relationship so a subsequent request for the data from the computer-accessible memory returns the data in combination with the identification of the patient.

7. The method of claim 1, wherein the standardized medical image transmission format is a DICOM standard.

8. The method of claim 1, wherein said receiving the patient identification comprises:
transmitting, over a communication network, a subset of patients registered at a healthcare facility for presentation to a user;
receiving, over the communication network, a specific patient selected by the user from the subset; and
establishing the identity of the patient as the specific patient selected by the user.

9. The method of claim 8, wherein said transmitting comprises transmitting the list of patients to the video capture device over the communication network.

* * * * *